(12) United States Patent  
Moser (10) Patent No.: US 6,490,928 B2
(45) Date of Patent: Dec. 10, 2002

(54) METHOD AND ARRANGEMENT FOR JUDGING THE FRICTION BEHAVIOR BETWEEN TWO COUNTER-RUNNING PARTNERS

(75) Inventor: Urs Moser, Zürich (CH)

(73) Assignee: Sulzer Markets and Technology AG, Winterhur (CH)

( * ) Notice: Subject to any disclaimer, the term of this patent is extended or adjusted under 35 U.S.C. 154(b) by 0 days.

(21) Appl. No.: 09/801,402

(22) Filed: Mar. 7, 2001

(65) Prior Publication Data

US 2001/0020391 A1 Sep. 13, 2001

(30) Foreign Application Priority Data

Mar. 7, 2000 (EP) .............................................. 00810191

(51) Int. Cl.⁷ .............................................. G01N 29/00
(52) U.S. Cl. ................................. 73/627; 73/7; 73/116; 73/657; 73/660
(58) Field of Search .......................... 73/627, 635, 657, 73/659, 660, 116, 120, 593, 7, 10

(56) References Cited

U.S. PATENT DOCUMENTS

| | | | | |
|---|---|---|---|---|
| 4,143,319 A | * | 3/1979 | Rouan ......................... 324/219 |
| 4,169,368 A | * | 10/1979 | Hendry ........................... 73/10 |
| 4,266,421 A | * | 5/1981 | McDougal ....................... 73/35 |
| 4,444,049 A | * | 4/1984 | Hitchcock .................. 73/119 A |
| 4,478,082 A | * | 10/1984 | Sato et al. ...................... 73/593 |
| 4,542,652 A | * | 9/1985 | Reuter et al. .................. 73/597 |
| 4,696,191 A | * | 9/1987 | Claytor et al. ................. 73/600 |
| 4,711,120 A | | 12/1987 | Kwun ....................... 73/119 R |
| 4,854,162 A | * | 8/1989 | Yerace et al. |
| 4,887,087 A | | 12/1989 | Clearwater .................... 342/61 |
| 5,406,854 A | * | 4/1995 | Wagner .................... 73/861.25 |
| 5,515,712 A | * | 5/1996 | Yunick ............................. 73/9 |
| 5,675,076 A | * | 10/1997 | Esch et al. .................... 73/116 |
| 5,739,417 A | * | 4/1998 | Grob et al. ................. 73/117.2 |
| 5,744,705 A | * | 4/1998 | Derouen et al. .............. 73/116 |
| 6,137,582 A | * | 10/2000 | Stedham ..................... 356/436 |

FOREIGN PATENT DOCUMENTS

| | | |
|---|---|---|
| DE | 3231587 A1 | 3/1983 |
| DE | 1962669 C1 | 8/1997 |
| EP | 0706039 A1 | 4/1996 |
| EP | 0738901 A2 | 10/1996 |
| EP | 1006271 A2 | 6/2000 |
| GB | 2154277 A | 9/1985 |

OTHER PUBLICATIONS

Patent Abstracts of Japan, vol. 013, No. 422 (P–933), Sep. 20, 1989, & JP 01 153934 A (Mitsubishi Heavy Ind Ltd.), Jun. 16, 1989, Abstract.
Patent Abstracts of Japan, vol. 010, No. 282 (P–500), Sep. 25, 1986, & JP 61 102508 (Toyota Motor Corp; others: 01.), May 21, 1986, Abstract.
Patent Abstracts of Japan, vol. 1999, No. 08 (P–500), Jun. 30, 1999, & JP 11 072132 A (Japan Radio Co Ltd), Mar. 16, 1999, Abstract.

* cited by examiner

*Primary Examiner*—Hezron Williams
*Assistant Examiner*—Jacques M Saint-Surin
(74) *Attorney, Agent, or Firm*—Townsend and Townsend and Crew LLP (57) ABSTRACT

A method and apparatus is proposed for judging the friction behavior between two counter-running partners, each of which has a contact surface, with the one contact surface moving along the other contact surface in the operating state. One of the contact surfaces is charged with ultrasonic signals (UI; UW), ultrasonic signals which are reflected by the contact surface are received as echo signals (ES), the echo signals (ES) are supplied to an evaluation unit as received signals, the Doppler shift of the received signals is determined by means of the evaluation unit, and the friction behavior between the counter-running partners is judged by means of the Doppler shift.

14 Claims, 5 Drawing Sheets

METHOD AND ARRANGEMENT FOR JUDGING THE FRICTION BEHAVIOR BETWEEN TWO COUNTER-RUNNING PARTNERS

The invention relates to a method and an arrangement for judging the friction behavior between two counter-running partners, each of which has a contact surface, with the one contact surface moving along the other contact surface in the operating state.

There are numerous machines and systems in which two counter-running partners which are moved relative to one another for journalling, guiding or sealing off are provided which slide along one another during operation in order to perform the journalling, guiding or sealing function.

In internal combustion engines with reciprocating pistons for example the piston rings which are provided at the piston move along the working surface of the cylinder, which represents their counter-running partner. Furthermore, for sealing off, journalling and guiding the piston rod in reciprocating piston combustion engines, e.g. compressors, packings are usually used which are fixed with respect to the housing and which have a plurality of rings which slide on the piston rod as counter-running partner. Also, in bearings or slide ring sealings for journalling and sealing off rotating shafts, e.g. in pumps, two counter-running partners also move frictionally along one another. In this, one of the counter-running partners is rotationally fixedly connected to the rotating shaft and the other is rotationally fixed relative to the stationary part of the machine.

Common to all these examples is that the cooperation between the counter-running partners, which are moved relative to one another, is based on the friction between the counter-running partners. The counter-running partners can form either a dry-operated or a lubricated frictional system. In dry-operated systems, for example dry-operated piston compressors, no external lubrication is provided and a solid lubricant is usually embedded in at least one of the counter-running partners. In lubricated frictional systems, for example internal combustion engines, a fluid external lubricant, for example an oil or another liquid, is typically provided which forms a lubricating film between the counter-running partners.

The determination and monitoring by measurement of the friction between two counter-running partners during operation is as a rule possible only indirectly, for example via the arising wear. For large diesel engines, like the one used for example as drive aggregates for ships or in stationary plants for generating electricity, for example in EP-A-706 039 an inductive measurement principle is proposed by means of which the wear state of a specially manufactured piston ring can be determined by measurement. With measurements of this kind however only wear which has already arisen can be determined. It is however desirable to be able to judge the friction behavior between the counter-running partners during operation, since abnormalities or changes in the running behavior of the counter-running partners can be detected significantly earlier on the basis of changes in the friction behavior than on the basis of the wear which has already arisen. Severe and expensive damages, for example piston binding or abnormally high wear values, can thereby be avoided substantially more effectively.

An object of the invention is therefore to propose a method and an arrangement by means of which the friction behavior between two counter-running partners can be judged during operation and as rapidly as possible. The method and the arrangement should in particular be suitable for judging the friction behavior between the piston rings and the cylinder barrel in an internal combustion engine, especially in a large diesel engine. Furthermore, the method and the arrangement should also be suitable for counter-running partners which rotate relative to one another during operation, for example slide ring sealings.

The subjects of the invention satisfying these objects in regard to method and apparatus are characterized by the features of the independent claim of the respective category.

Thus in accordance with the invention a method and an arrangement are proposed for judging the friction behavior between two counter-running partners, each of which has a contact surface, with the one contact surface moving along the other contact surface in the operating state. The method in accordance with the invention comprises the following steps: one of the contact surfaces is charged by ultrasonic signals; ultrasonic signals which are reflected by the contact surface are received as echo signals; the echo signals are supplied to an evaluation unit as received signals; the Doppler shift of the received signals is determined by means of the evaluation unit; and the friction behavior between the counter-running partners is judged by means of the Doppler shift.

The arrangement in accordance with the invention comprises an ultrasonic converter and an evaluation unit, with the ultrasonic converter charging one of the contact surfaces with ultrasonic signals, receiving ultrasonic signals which are reflected from the contact surface as echo signals and supplying the latter to the evaluation unit as received signals, and with the evaluation unit comprising evaluation means which determines the Doppler shift of the received signals and determines a characteristic value for judging the friction behavior between the counter-running partners by means of the Doppler shift.

The invention is based on the observation that the friction between two counter-running partners causes a Doppler shift in ultrasonic signals with which the contact surface of a counter-running partner is charged which is sufficiently strongly pronounced in order to enable a judging of the friction behavior. Changes in the friction in particular lead to significant changes in the spectrum of the Doppler shift. Thus if an increase in the friction between the counter-running partners arises during operation, for example as a result of a faulty lubrication, or a reduction of the friction, for example through a damaged or worn piston ring, then this can be detected on the basis of the Doppler shift and corresponding countermeasures can be taken in time in order to avoid severe resultant damages.

Since the ultrasonic converter must have no direct physical contact with the contact surface the method in accordance with the invention and the arrangement in accordance with the invention are also suitable for judging the friction behavior at locations which are inaccessible or are difficult of access, e.g. for judging the friction behavior between a piston ring and the cylinder barrel in an internal combustion engine. In addition the method and the arrangement respectively can be used without problem during the normal operating state of a machine, so that a judging and thus a monitoring of the momentary friction behavior between the counter-running partners are possible as if it were on-line.

It turned out that an increase in the friction between the counter-running partners leads in particular to an amplification or to an increase respectively of those components of the Doppler shift which lie at high frequencies. Therefore, preferably only those frequencies in the frequency spectrum for the Doppler shift which are greater than a predetermined threshold value are taken into account for the judging of the friction behavior.

For reasons of as simple an evaluation as possible it is preferred when contact surface is charged with the ultrasonic signals substantially perpendicularly to the direction of the relative movement of the two counter-running partners.

In accordance with a first exemplary embodiment of the invention the contact surface is charged with ultrasonic pulses, which means that the ultrasonic converter emits wave packets as ultrasonic pulses at regular intervals.

In accordance with a second exemplary embodiment the contact surface is charged by a continuous ultrasonic wave, which means that in this method, which is usually called the CW (continuous wave) method, the ultrasonic converter does not emit the ultrasonic signals in the form of individual discrete pulses, but rather permanently as a continuous wave. In the CW method the ultrasonic converter preferably comprises two converter elements, one of which serves for emitting the ultrasonic signal and the other for receiving the echo signals. The two converter elements are arranged in such a manner that the emitter field of the first converter element and the reception field of the second converter element at least partly overlap. This can be realized for example in that the two converter elements are arranged adjacently and where appropriate with a slight inclination with respect to one another, so that their axes intersect at the contact surface. The two converter elements can however also be arranged concentrically.

A preferred use of the method in accordance with the invention or of the arrangement in accordance with the invention is the use for judging the friction behavior between a piston ring and its counter-running partner in an internal combustion engine, in particular in a large diesel engine, e.g. in the main engine of a ship.

Further advantageous measures and preferred embodiments of the invention result from the subordinate claims.

In the following the invention will be explained in more detail both in regard to the apparatus and to the method with reference to exemplary embodiments and with reference to the drawings. Shown in the schematic drawings are.

Figure 1:
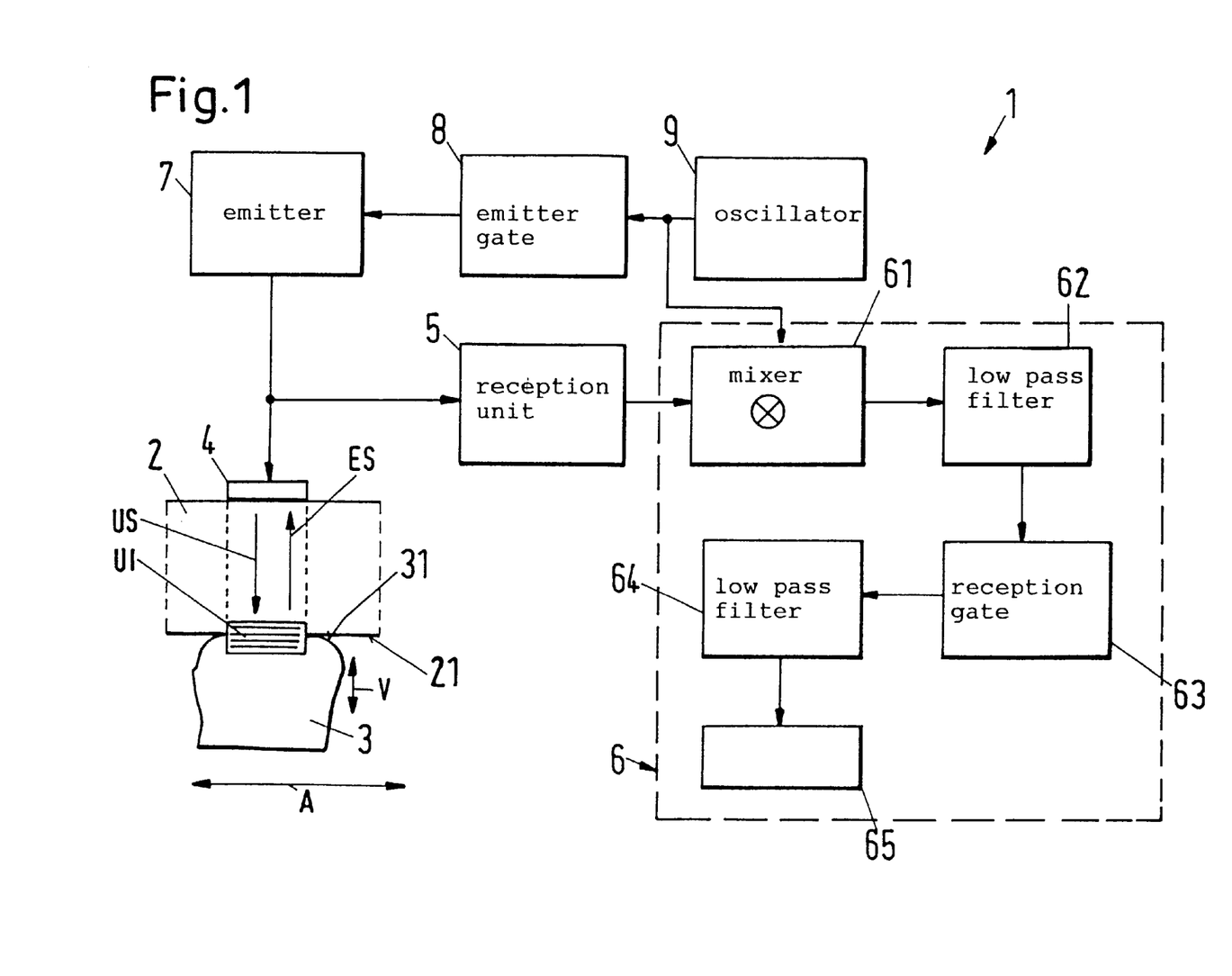
FIG. 1: a block diagram for illustrating a first exemplary embodiment of the invention.

The block diagram in FIG. 1 illustrates a first exemplary embodiment of the method in accordance with the invention or of the apparatus in accordance with the invention respectively, for judging the friction behavior between two counter-running partners 2, 3, each of which has a contact surface 21 and 31 respectively, with the one contact surface 31 moving along the other contact surface 21 in the operating state, as the double arrow A in FIG. 1 indicates. The arrangement is designated in its entirety with the reference symbol 1.

In this, the term "counter-running partners" is intended to mean components of a machine which slide along one another with friction in the operating state of the machine and thus form a frictional system. The counter-running partners 2, 3 can form a dry-operated system, which means that no external lubricant is provided between the counter-running partners 2, 3; or the counter-running partners 2, 3 form a lubricated frictional system, which means that in the normal operating state an external lubricant, for example a lubrication oil film or another lubricant or sliding means, is present between the contact surfaces 21, 31 of the counter-running partners 2, 3.

The movement of the counter-running partners 2, 3 relative to one another which is indicated by the arrow A can be a linear movement, such as arises for example as an oscillatory stroke movement in a reciprocating piston combustion engine, or also a rotational movement, such as for example arises in a seal of a rotating shaft.

In the following, several examples of counter-running partners will be named in a non exhaustive listing: a piston ring and the cylinder wall or the cylinder liner respectively, in an internal combustion engine, a piston ring and the cylinder wall in a lubricated or a dry-operated piston compressor, the rings of a packing and the piston rod in a reciprocating piston combustion engine, a rotating shaft and a bearing sleeve for this shaft, the slide ring and the stator in a slide ring sealing for sealing off a rotating shaft.

In the following description reference is made with exemplary character to the application of an internal combustion engine, especially a large diesel engine. The explanations however also hold in an analogous manner for all other counter-running partners 2, 3.

In a large diesel engine a piston moves in an oscillatory manner in a cylinder liner which is arranged in a cylinder and which is also designated simply as a liner. As a rule a plurality of piston rings are provided at the piston which move along the inner wall of the liner in the stroke movement of the piston, with a lubricating film being provided between the liner and the piston rings.

With reference to FIG. 1 the cylinder liner is the one counter-running partner 2, which is in this case stationary; and the inner wall of the liner forms the one contact surface 21. The other counter-running partner 3 is a piston ring, the radial outer boundary surface of which forms the other contact surface 31, which moves along the contact surface 21 during operation.

The arrangement 1 comprises an ultrasonic converter 4, which is arranged in such a manner that it can charge the contact surface 31 with ultrasonic signals UI, a reception unit 5 and an evaluation unit 6. For the control of the ultrasonic converter 4 an oscillator 9, an emitter gate 8 and an emitter 7 are provided. The evaluation unit 6 comprises a mixer 61, a low pass filter 62, a reception gate 63, a further low pass filter 64 and a signal analyzer 65.

In the case of an internal combustion engine, the ultrasonic converter 4 is for example arranged at the cylinder or at the cylinder liner respectively or in a cut-out which is provided in the cylinder or in the liner respectively and which preferably extends in the radial direction, which means perpendicularly to the longitudinal axis of the cylinder. The ultrasonic converter 4 is arranged in such a manner that the ultrasonic signals which are generated by it are emitted substantially in the radial direction and thus are incident onto the contact surfaces 21, 31 perpendicular to the direction A of the relative movement of the two counter-running partners 2, 3.

In the exemplary embodiment in accordance with FIG. 1 the ultrasonic converter 4 is operated in a pulsed manner, which means that it emits an ultrasonic wave packet at regular intervals. In FIG. 1 an ultrasonic pulse UI of this kind is illustrated symbolically; its direction of propagation is indicated by the arrow US. The ultrasonic pulse UI propagates through the counter-running partner 2 and is incident onto the contact surface 31 of the counter-running partner 3. The contact surface 31 reflects a portion of the ultrasonic pulse UI and thus generates an echo signal EG, which is received and evaluated in the evaluation unit 6.

The friction between the counter-running partners 2, 3, which are moved relative to one another, causes vibrations of the counter-running partners 2, 3. These vibrations have a velocity component which is directed towards the ultrasonic converter 4 and which is indicated in FIG. 1 by the double arrow V. As a result of this velocity component V of the vibrations the echo signal ES which is generated by the contact surface 31 through reflection has a frequency shift which is based on the Doppler effect and which is designated as a Doppler shift. In the evaluation unit 6 the Doppler shift is determined and the friction is judged on the basis of the latter.

This method proves to be very sensitive. Even though the vibrations which are caused by the friction typically have amplitudes which are only in the micron range, and are thus smaller by a factor on the order of magnitude of $10^3$ than the wave length of the ultrasonic signals which are typically used here, the Doppler shift can be separated out of the echo signals.

If now the friction between the counter-running partners 2, 3 changes, then this leads to changes in the frequency and/or the amplitude of the vibrations. A change in the Doppler shift results from this which has proved to be strong enough to be detected. In this way, a judging of the friction behavior between the counter-running partners 2, 3 on the basis of the Doppler shift is possible.

Figure 2:
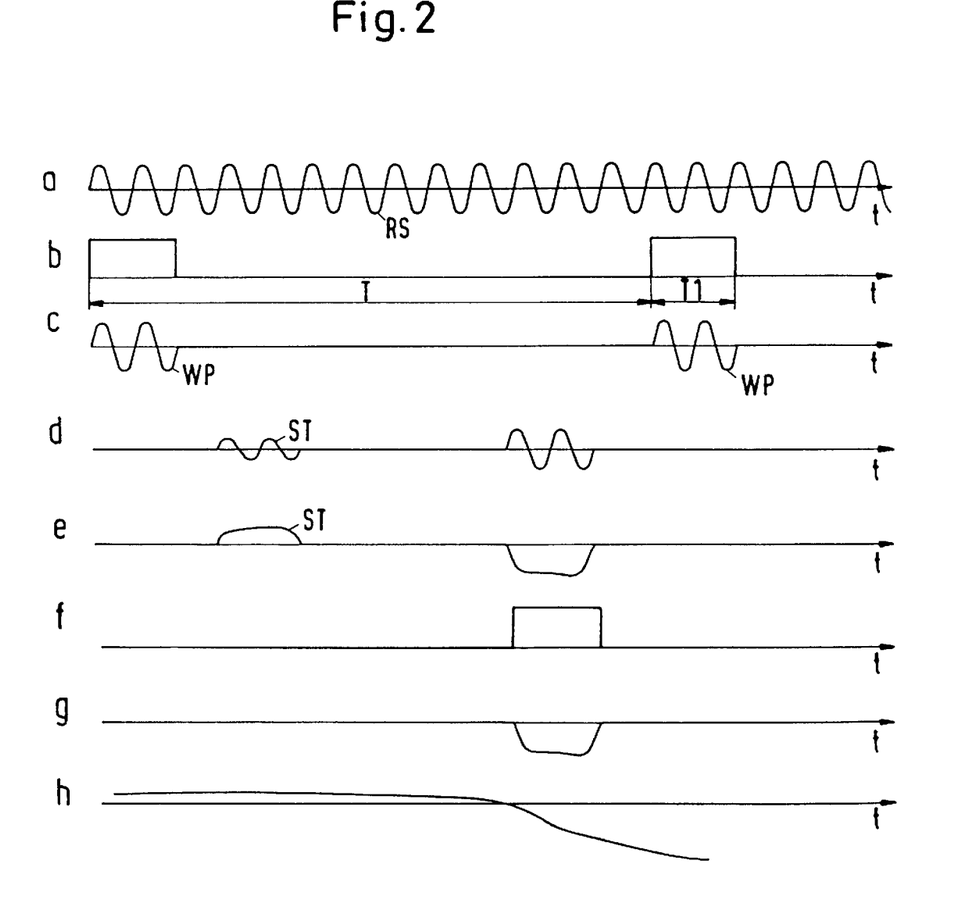
FIG. 2: various signals as functions of time.
Figure 3:
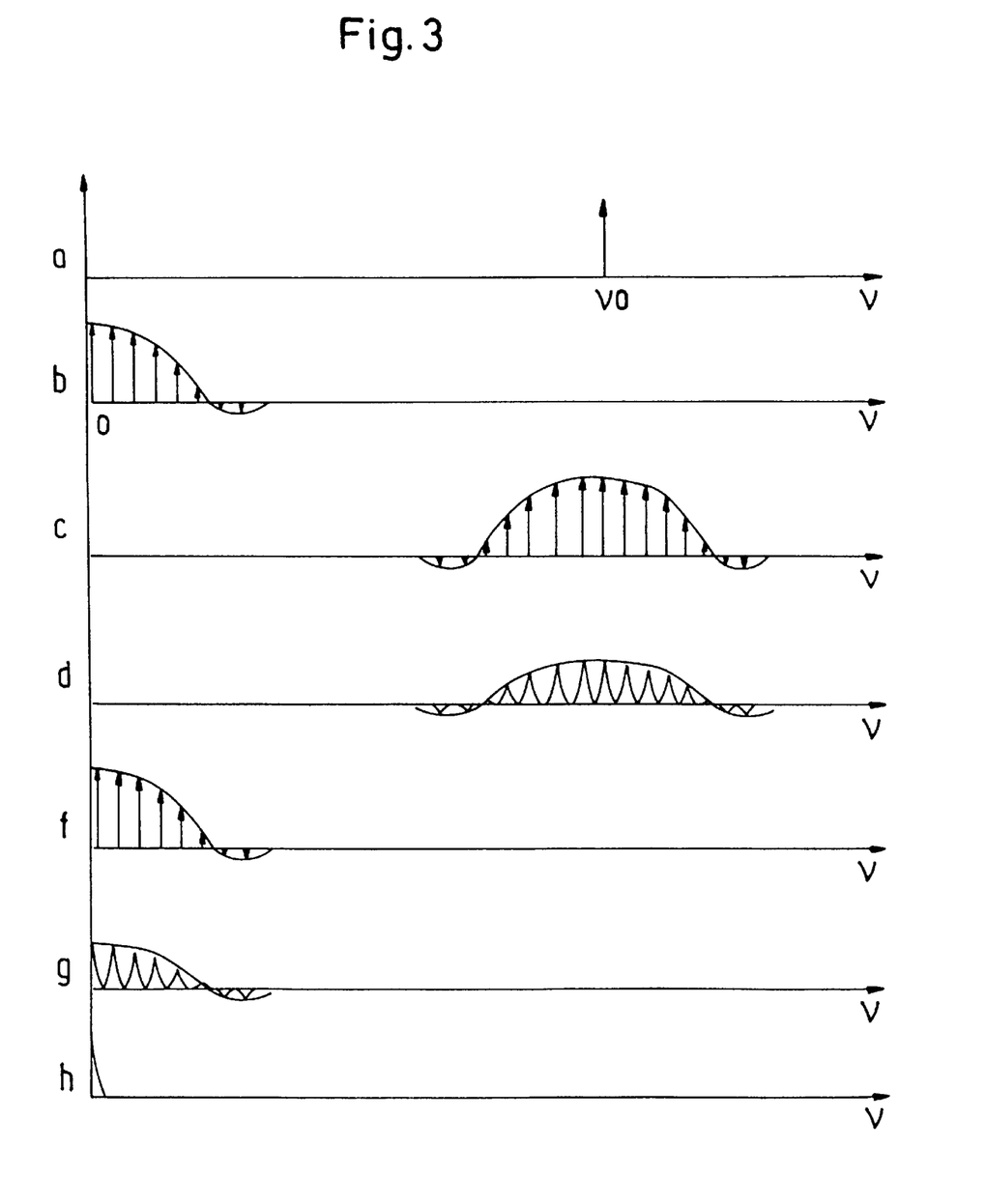
FIG. 3: some of the signals of FIG. 2 in frequency space.

In the following the essential steps for the exemplary embodiment which is illustrated in FIG. 1 and which works with pulsed ultrasonic signals will now be explained in more detail. In this, reference is also made to FIGS. 2 and 3. FIG. 2 shows various signals in a time domain, which means as functions of time t, that remain to be explained, and FIG. 3 shows corresponding signals in a frequency domain, which means as functions of the frequency ν.

The oscillator 9, which is preferably a quartz-stabilized oscillator, generates a reference signal RS with a constant frequency $v_0$ of for example 2 MHz. This reference signal RS is illustrated in diagram a of FIGS. 2 and 3 respectively. The reference signal RS is transmitted to the emitter gate 8, which represents an electronic switch which "cuts out" several oscillations, for example four, out of the reference signal and produces a wave packet WP in this manner. The emitter gate 8 is periodically activated, that is, opened, at equal time intervals T (e.g. every 100 microseconds) for a predetermined time period T1. This is illustrated in the diagrams b in FIGS. 2 and 3. At the output of the emitter gate 8 wave packets, which are illustrated in the diagrams c in FIGS. 2 and 3, then arise in periodical, always equal time intervals T. In time space (FIG. 2), diagram c results from multiplication of the diagrams a and b.

The wave packets WP are transmitted to the emitter 7, which amplifies them and supplies them to the ultrasonic converter 4, which usually has at least one piezoelectric sound converter. The ultrasonic converter 4 transforms the wave packets WP into ultrasonic pulses UI, which are reflected at the contact surface 31 of the counter-running partner 3 as described above. In this the spectrum of the emitted wave packet, which is illustrated in FIG. 3, diagram c, is frequency modulated at the vibrating contact surface 31 of the counter-running partner 3. Each spectral component is therefore broadened (FIG. 3, diagram d). The resulting echo signal reaches the ultrasonic converter 4, which converts the echo signal into an electrical reception signal. The received signals are illustrated in the diagrams d of FIGS. 2 and 3. In FIG. 3, diagram d it can be recognized that the spectrum of the received signal is modulated through the Doppler effect. The stationary echo, which arises through reflection at the contact surface 21, is not or only very slightly frequency modulated and is not illustrated in the diagram d of FIG. 3. In FIG. 2, diagram d an undesirable interference signal ST is also illustrated which for example arises through reflections from regions other than the boundary layer between the two counter-running partners 2, 3.

The received signals are supplied to the reception unit 5, amplified there and then transmitted to the evaluation unit 6. Since the frequency shift caused by the Doppler effect, which typically amounts only to about up to several hundred Hertz, is relatively small in comparison with the frequency of the reference signal RS, the received signal is mixed with the reference signal RS in the mixer 61 of the evaluation unit 6 for demodulation. This corresponds in the time domain to a multiplication of the reference signal RS by the received signal. Through this the sum and difference frequencies of the reference signal RS and the received signal are available at the output of the mixer 61. The higher frequency sum frequencies are suppressed by the following low pass filter 62. The remaining difference frequencies represent the Doppler shift. In this way the Doppler shifts can be separated out of the received signal and can thus be determined. The resultant signal after passage through the mixer 61 and the low pass filter 62 is shown in diagram e of FIG. 2. It can be recognized that the interference signal ST is still present in the signal. The elimination of the interference signal ST can be carried out as follows.

In the exemplary embodiment in accordance with FIG. 1 ultrasonic pulses UI are used, which means that it is a matter of a pulsed system. Since the distance between the ultrasonic converter 4 and the boundary layer between the counter-running partners 2, 3 as well as the velocity of sound in the medium to be traversed have substantially constant values, which are known or can be determined, the travel time of the sound pulses from the ultrasonic converter to the boundary layer and back can be determined. This enables a spatially resolved measurement in that a time window is defined for the received signals, the temporal distance of which from the time point of the emission of the ultrasonic pulse UI corresponds to the required travel time to the boundary layer and back. Then only those echo or received signals respectively are taken into account which are measured by the ultrasonic converter 4 within this time window. This time window is realized through the reception gate 63 and is illustrated in the diagrams f of FIGS. 2 and 3. In the frequency domain (FIG. 3, diagram f) the spectrum of the reception gate 63 corresponds to the spectrum of the emitter gate 8. Through the reception gate 63 the spectrum which is illustrated in diagram d of FIG. 3 is convoluted with the spectrum of the reception gate 63 in the frequency domain (FIG. 3 diagram f), through which the repetitions of the components which have arisen through the frequency modulation (Doppler shift) are laid one upon the other. The reception gate 63 contributes substantially to the elimination of undesirable interference signals ST. In the diagrams g of FIGS. 2 and 3 the signal is illustrated after passage through the reception gate 63. In particular in FIG. 2, diagram g it can be clearly recognized that the interference signal ST has been eliminated.

As a result of the pulsed operation the ultrasonic system described here is a sampling system, with the sampling frequency being equal to the repetition frequency of the ultrasonic pulses. The latter is the inverse of the temporal distance T between two successive ultrasonic pulses UI. In order to reconstruct the frequency spectrum for the Doppler shift, therefore, the signal which is illustrated in diagram g of FIG. 3 must be filtered with the low pass filter 64, which serves as a Nyquist filter, which means that at the maximum the limiting frequency of the low pass filter 64 is as large as half the repetition frequency of the ultrasonic pulses, so that all higher frequencies are substantially eliminated. The thus reconstructed frequency spectrum for the Doppler shift relative to the frequency of the ultrasonic pulses (reference frequency RS) is illustrated in the diagram h of FIG. 3 and will be designated as the Doppler spectrum. The diagram h in FIG. 2 shows a section of the corresponding signal in the time domain.

Since the frequencies of the vibrations of the counter-running partner 3 typically lie in the range of several kilohertz, and are thus very much lower than the frequency of the emitted ultrasonic signal (for example 2 MHz), and in addition the amplitudes of the vibrations, which usually amount to less than 100 microns, the shape of the Doppler spectrum can be estimated in a simple way.

After the Doppler spectrum has been determined, it is transmitted for further evaluation to the signal analyzer 65. This evaluation will be explained further below in connection with FIGS. 5 and 6.

Figures 4, 8:
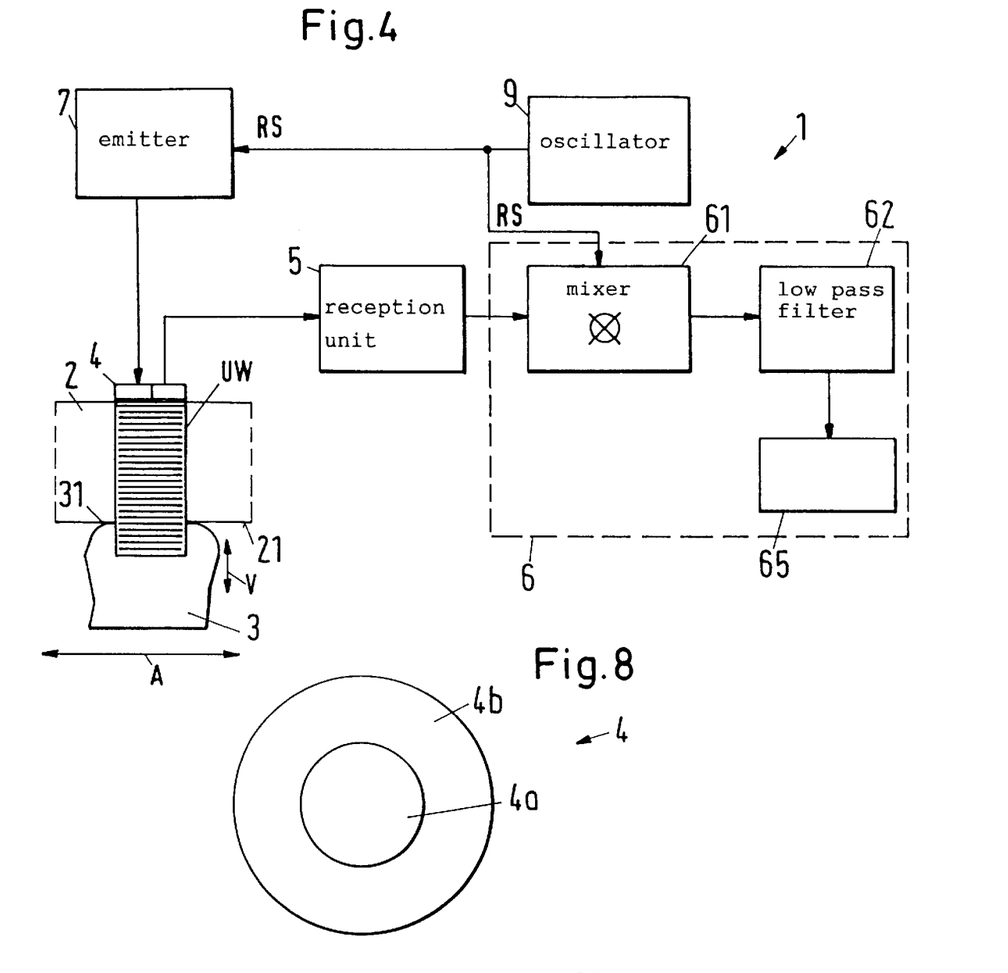
FIG. 4: a block diagram for illustrating a second exemplary embodiment of the invention.
FIG. 8: a plan view of a design of the ultrasonic converter with two converter elements.

FIG. 4 shows a block diagram of a second exemplary embodiment of the invention in an illustration analogous to FIG. 1. In this, parts which are identical or equivalent in function are provided with the same reference symbols, which have already been explained.

The essential difference between the first and the second exemplary embodiment lies in that the contact surface 31 is charged with a continuous ultrasonic wave UW in the second exemplary embodiment. It is thus not a matter of a pulsed method here, but of a continuous one, which is designated as a continuous wave method (CW method). Otherwise the explanations with respect to the first exemplary embodiment also hold analogously for the second exemplary embodiment. The CW method, which is technically simpler than the pulsed method, is suitable for applications in which no spatial or distance resolution of the ultrasonic signals or of the echo signals respectively is necessary, for example when no or only slight interference signals are superimposed on the echo signals.

In the CW method the ultrasonic converter 4 preferably comprises two converter elements 4a, 4b (see FIG. 8), one of which serves for emitting the ultrasonic signal and the other for receiving the echo signals. The two converter elements 4a, 4b are arranged in such a manner that the emitted field of the first converter element 4a and the reception field 4b of the second converter element at least partly overlap. This can for example be realized in that the two converter elements 4a, 4b are arranged adjacently and where appropriate with a slight inclination relative to one another, so that their axes intersect at the contact surface. The term axes means the main directions of the sound propagation, that is, the direction in which an ultrasonic signal is emitted from the converter element. The two converter elements 4a, 4b can however be arranged concentrically. Such an arrangement of the ultrasonic converter 4 is illustrated in a plan view in FIG. 8. The first converter element 4a is designed to be circular and the second converter element 4b ring-shaped, with the second converter element 4b surrounding the first converter element 4a. In principle it is irrelevant which one of the two converter elements 4a, 4b is used for emitting the ultrasonic signal and which for receiving the echo signals.

Through the measure of providing two converter elements 4a, 4b at the ultrasonic converter 4 the emitter is decoupled from the receiver in order that the stronger emitter signals do not "congest" the receiver.

The oscillator 9 (FIG. 4) generates the continuous reference signal RS with constant frequency. The reference signal RS is amplified in the emitter 7 and then supplied to the ultrasonic converter 4. The converter element 4a of the ultrasonic converter 4 transforms the signal and emits it as a continuous single-frequency ultrasonic wave UW. The ultrasonic wave passes through the counter-running partner 2 and is reflected at the contact surface 31 of the counter-running partner 3, through which the echo signal is generated. In this reflection the ultrasonic wave is frequency modulated by the vibrations (indicated by the arrow A). The frequency modulated echo signal is received by the converter element 4b of the ultrasonic converter 4, transformed into an electrical reception signal and then transmitted to the reception unit 5.

The latter amplifies the received signal and transmits it to the evaluation unit 6. In the evaluation unit 6 the received signal is demodulated by the mixer 61 in a manner analogous to that explained above in that it is multiplied by the reference signal RS. Then the low pass filter 62 eliminates the sum frequencies which result from the mixing. The remaining difference frequencies represent the Doppler spectrum, which is passed on to the signal analyzer 65 for further evaluation.

Figure 5:
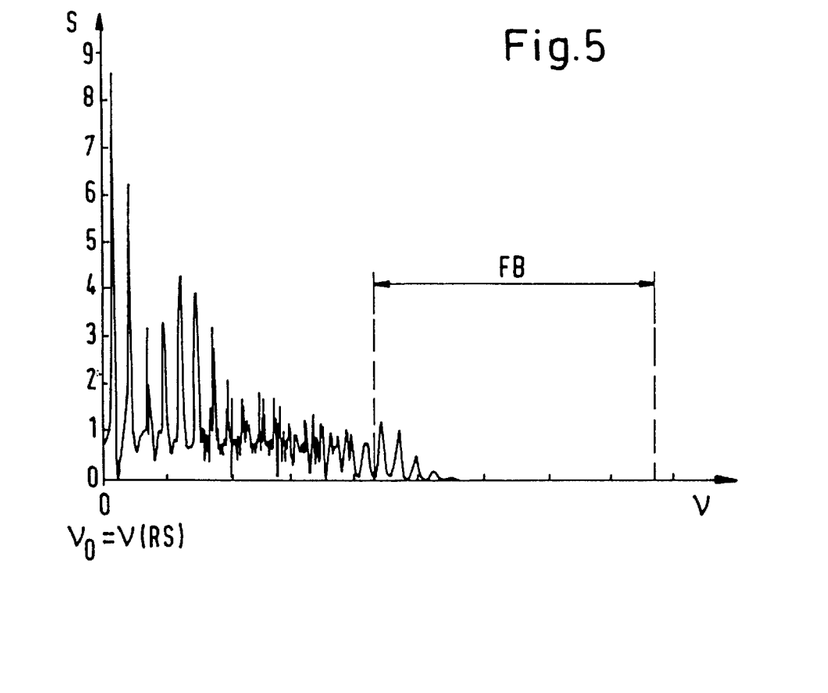
FIGS. 5, 6: two frequency spectra of the Doppler shift for friction of different strengths.
Figure 6:
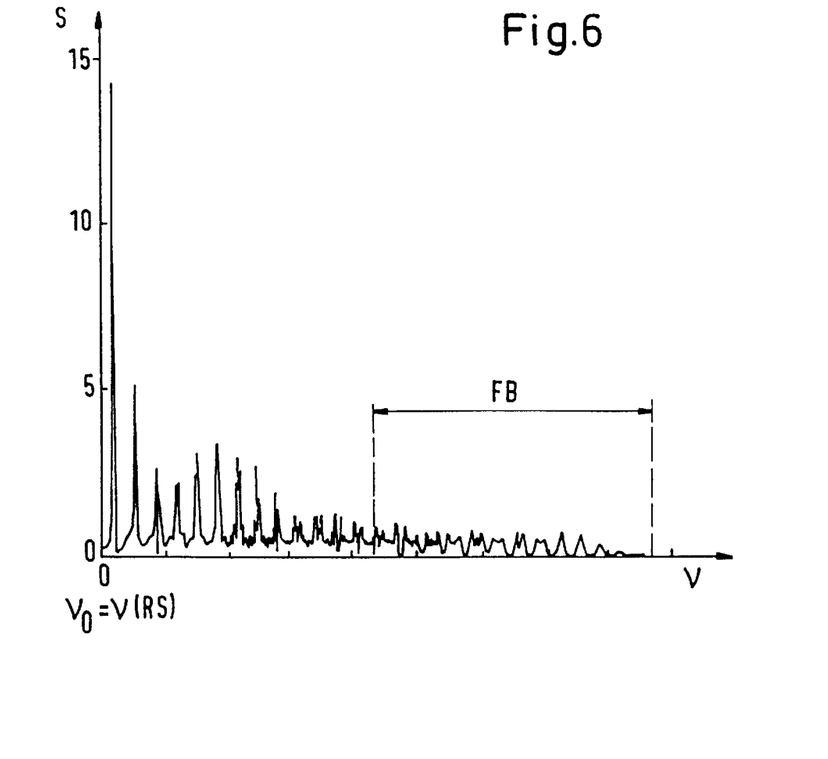

Two typical Doppler shifts are illustrated in FIGS. 5 and 6. They correspond in each case to an enlarged illustration of the Doppler spectrum which is illustrated in a simplified manner in FIG. 3, diagram h. To the right in each case the frequency v is plotted relative to the frequency $v_0$ of the reference signal RS, which means that the zero point of the frequency axis is the frequency $v_0$=v(RS) of the reference signal RS. Upwardly the signal intensity is in each case plotted in random units.

Since it makes no difference qualitatively whether the Doppler spectrum has been determined by means of the pulsed method (first exemplary embodiment) or by means of the CW method as long as the Doppler shifts are less than the Nyquist frequency (which is generally the case), the following explanations hold for both exemplary embodiments.

The Doppler spectrum in FIG. 6 corresponds to a state in which the friction between the two counter-running partners 2, 3 is stronger than in the state which corresponds to the Doppler spectrum in FIG. 5. With increasing frequency the vibration amplitudes and/or the vibration frequencies increase rapidly. This leads to a significant increase in the signal intensities of the higher frequencies in the Doppler spectrum, as can be clearly recognized through a comparison of FIGS. 5 and 6. This means that the friction between the two counter-running partners 2, 3 has a direct influence on the Doppler spectrum, so that the friction behavior between the two counter-running partners can be judged on the basis of the Doppler spectrum.

For example in the normal operating state, which means with normal friction behavior between the counter-running partners 2 and 3, Doppler spectra are received which are characteristic for this normal operating state and serve as reference spectra. Doppler spectra which are representative for the momentarily acting friction between the counter-running partners 2 and 3 are then determined continually or at predeterminable intervals during the operation. These Doppler spectra are then in each case compared with the reference spectra, through which it can be determined whether the friction has changed significantly relative to the normal value. Thus for example an excessively large friction can be detected as if it were on-line during operation and countermeasures can be taken in time to avoid resultant damages.

Figure 7:
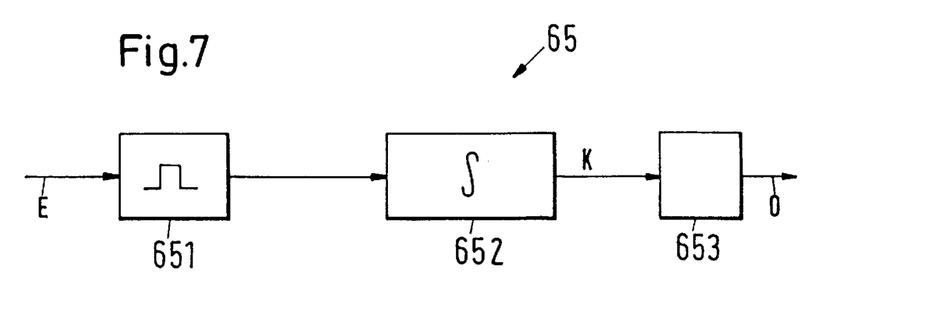
FIG. 7: a block diagram of a design of the signal analyzer.

FIG. 7 shows in a block diagram a possible design of the signal analyzer 65. It comprises a bandpass filter 651, a computation unit 652 and a threshold value detector 653. The respective determined Doppler spectrum is transmitted to the signal analyzer 65, as indicated by the arrow in FIG. 7. The bandpass filter 651 filters a predeterminable frequency range FB (see FIGS. 5 and 6) out of the Doppler spectrum. This frequency range FB is chosen such that it contains the frequencies of the Doppler spectrum at which significant changes arise when the friction between the counter-running partners 2, 3 changes. In the case of the Doppler spectra which are illustrated in FIGS. 5 and 6 for example the middle frequency range FB is suitable, which is bounded in each case by the two broken lines and corresponds to frequencies from 2 kHz to 4 kHz.

After the frequency range FB has been filtered by means of the bandpass filter 651, the computation unit 652 determines a characteristic value K for the judging of the friction behavior, for example through an integration of the Doppler spectrum over this frequency range FB. The characteristic value K is representative for the signal power in the filtered out frequency range. The computation unit 652 transmits the characteristic value K to the threshold value detector 653. When the threshold value detector determines that the friction which is represented by the characteristic value K exceeds a threshold value or lies outside a permissible range, it for example triggers an alarm, as is indicated by the arrow O in FIG. 7. The threshold value or values for the characteristic value K can e.g. be determined experimentally.

In principle it is irrelevant whether the signal power is determined from the Doppler shift in the time domain, for example via an auto-correlation function, or in the frequency domain, for example via a power spectrum. In the time domain, the characteristic value K can for example be determined in that the signal power of the signal which is passed by the bandpass filter 651, which can for example be determined through squaring the signal, is averaged over a predeterminable integration time. An evaluation of this kind can also be simply realized with analog circuitry.

Naturally differentiated evaluations of the Doppler spectrum are also possible, for example such which take into account the shape of the Doppler spectrum. It is also possible to digitalize the Doppler spectrum in order to carry out a differentiated evaluation.

Embodiments are naturally also possible for the pulsed method in which the ultrasonic converter 4 comprises a plurality of different converter elements; for example the emission of the ultrasonic signals can take place with a converter element which is different from that for receiving the echo signals.

As already mentioned, the invention is also suitable for counter-running partners which execute a rotational movement relative to one another, such as is for example the case in slide ring sealings at rotating shafts. Then the rotating contact surface, usually the jacket surface of a circular disc or of a cylinder, is charged, preferably from the radial direction, that is, perpendicularly to the direction of the relative movement of the two counter-running partners, by the ultrasonic signals.

Naturally it is also possible in principle to charge the corresponding contact surface with ultrasonic signals at an oblique angle, both in the case of linear, straight-line movements and also in rotational movements of the counter-running partners relative to one another.

Thus through the invention a method and an apparatus are proposed, by means of which the friction between two counter-running partners 2, 3 can be judged and thus also monitored very rapidly, as if it were on-line, during operation.

What is claimed is:

1. Method for judging the friction behavior between two counter-running partners, each of which has a contact surface, with one of the contact surfaces moving along the other one of the contact surfaces during operation, the method comprising:
    a) charging one of the contact surfaces with ultrasonic signals,
    b) receiving ultrasonic signals which are reflected by one of the contact surfaces as echo signals,
    c) supplying the echo signals to an evaluation unit as received signals,
    d) determining a Doppler shift of the received signals, and
    e) judging the friction between the counter-running partners by means of the Doppler shift.

2. Method in accordance with claim 1 including mixing the received signals for demodulation with a reference signal having the same frequency as the ultrasonic signals with which the contact surface is charged.

3. Method in accordance with claim 1 wherein the step of determining includes determining a frequency spectrum for the Doppler shift relative to a frequency of the ultrasonic signals.

4. Method in accordance with claim 1 including taking into account only frequencies in the frequency spectrum for judging the friction which are greater than a predetermined threshold value.

5. Method in accordance with claim 1 including determining a characteristic value for judging the friction which is representative for the signal power of the received signals in a predeterminable frequency range.

6. Method in accordance with claim 1 wherein the contact surface is charged with the ultrasonic signals substantially perpendicularly to a direction of relative movement of the counter-running partners.

7. Method in accordance with claim 1 wherein the contact surface is charged with ultrasonic pulses.

8. Method in accordance with claim 1 including charging one of the contact surfaces with a continuous ultrasonic wave.

9. Arrangement for judging the friction behavior between two counter-running partners, each of which has a contact surface, one of the contact surfaces moving along the other one of the contact surfaces during operating the arrangement comprising an ultrasonic converter and an evaluation unit, the ultrasonic converter charging one of the contact surfaces with ultrasonic signals, receiving ultrasonic signals as echo signals which are reflected by the contact surface, the evaluation unit receiving the received signals and comprising an evaluator for determining a Doppler shift of the received signals and with the Doppler shift generating a characteristic value for judging the friction between the counter-running partners.

10. A method in accordance with claim 1 wherein one of the two counter-running partners comprises a piston ring in an internal combustion engine, and wherein judging comprises judging the friction between the piston ring and the other counter-running partner.

11. A method according to claim 10 wherein the internal combustion engine comprises a large diesel engine.

12. An arrangement according to claim 9 wherein one of the counter-running partners comprises a piston ring in an internal combustion engine.

13. An arrangement according to claim 12 wherein the internal combustion engine comprises a large diesel engine.

14. A method for judging friction between first and second counter-running partners having first and second contact surfaces in mutual contact which move relative to each other comprising directing ultrasonic signals onto at least one of the contact surfaces, receiving ultrasonic signals reflected by the at least one contact surface, determining a Doppler shift between the ultrasonic signals directed to the at least one contact surface and received from the at least one contact surface, and from the Doppler shift between the directed and received ultrasonic signals judging the friction encountered between the running partners.

* * * * *